US012601013B2

(12) United States Patent (10) Patent No.: US 12,601,013 B2
Cai et al. (45) Date of Patent: Apr. 14, 2026

(54) MOLECULAR MARKERS FOR IDENTIFYING ALLELE AT RICE-BLAST-RESISTANT PIK LOCUS OF RICE AND USE THEREOF

(71) Applicant: Institute of Food Crops, Hubei Academy of Agricultural Sciences, Wuhan (CN)

(72) Inventors: Haiya Cai, Wuhan (CN); Yonggang He, Wuhan (CN); Shuo Zhang, Wuhan (CN); Gang Liu, Wuhan (CN); Yanhao Xu, Wuhan (CN); Chunhai Jiao, Wuhan (CN); Aiqing You, Wuhan (CN); Lei Zhou, Wuhan (CN); Xingfei Zheng, Wuhan (CN)

(73) Assignee: Institute of Food Crops, Hubei Academy of Agricultural Sciences, Wuhan (CN)

( * ) Notice: Subject to any disclaimer, the term of this patent is extended or adjusted under 35 U.S.C. 154(b) by 785 days.

(21) Appl. No.: 18/054,125

(22) Filed: Nov. 9, 2022

(65) Prior Publication Data
US 2023/0183822 A1 Jun. 15, 2023

(30) Foreign Application Priority Data
Dec. 14, 2021 (CN) .......................... 202111532161.1

(51) Int. Cl.
*C12Q 1/68* (2018.01)
*C12Q 1/6895* (2018.01)
*C12Q 1/686* (2018.01)

(52) U.S. Cl.
CPC ........... *C12Q 1/6895* (2013.01); *C12Q 1/686* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 2004/0006788 A1* | 1/2004 | Wang | .................... | C07K 14/415 800/320.2 |
| 2006/0223136 A1* | 10/2006 | Kaku | ....................... | C12Q 1/32 435/484 |
| 2023/0183822 A1* | 6/2023 | Cai | ...................... | C12Q 1/6895 435/6.11 |

FOREIGN PATENT DOCUMENTS

| | | | | | |
|---|---|---|---|---|---|
| CN | 102618533 | A | * | 8/2012 | |
| CN | 102653760 | B | | 12/2012 | |
| CN | 104611332 | A | * | 5/2015 | |
| CN | 104789655 | A | * | 7/2015 | ........... C12Q 1/6895 |
| CN | 105543366 | A | * | 5/2016 | ........... C12Q 1/6895 |
| CN | 105907884 | A | * | 8/2016 | ........... C12Q 1/6895 |
| CN | 105925575 | A | * | 9/2016 | ........... C12Q 1/6895 |
| CN | 106048069 | A | * | 10/2016 | ........... C12Q 1/6895 |
| CN | 103060336 | B | * | 2/2017 | |
| CN | 104531717 | B | | 2/2017 | |
| CN | 108977568 | A | * | 12/2018 | ........... C12Q 1/6895 |
| CN | 107937600 | B | | 3/2021 | |
| CN | 112662804 | A | * | 4/2021 | |
| CN | 112695114 | A | | 4/2021 | |
| CN | 113999934 | A | * | 2/2022 | ........... C12Q 1/6895 |
| CN | 113744800 | B | | 6/2022 | |
| CN | 116640774 | A | * | 8/2023 | ........... C07K 14/415 |
| CN | 117778607 | A | * | 3/2024 | |
| JP | 4756334 | B2 | * | 8/2011 | |

OTHER PUBLICATIONS

CN102618533A_Description is English Translation of CN102618533A by Qianhua Pan et al. filed Mar. 8, 2012, pub. Aug. 1, 2012 (Year: 2012).*
CN104611332A_Description is English Translation of CN104611332A by Cai Haiya et al. filed Jan. 27, 2015, pub. May 13, 2015 (Year: 2015).*
CN104789655A_Description is English Translation of CN104789655A by Guo Tao et al. filed Mar. 23, 20152, pub. Jul. 22, 2015 (Year: 2015).*
CN103060336B_Description is English Translation of CN103060336B filed Oct. 21, 2011, pub. Feb. 22, 2017 (Year: 2017).*
CN105543366A_Description is English Translation of CN105543366A by Zhou Lei et al. filed Jan. 11, 2016, pub. May 4, 2016 (Year: 2016).*
CN105907884A_Description is English Translation of CN105907884A by Cai Haiya et al. filed Jul. 4, 2016, pub. Aug. 31, 2016 (Year: 2016).*
CN105925575A_Description is English Translation of CN105925575A by Xu Huanghan et al. filed Jul. 5, 2016, pub. Sep. 7, 2016 (Year: 2016).*

(Continued)

*Primary Examiner* — Gary Benzion
*Assistant Examiner* — Olayinka A Oyeyemi
(74) *Attorney, Agent, or Firm* — Mei & Mark LLP; Manni Li

(57) ABSTRACT

For molecular genetic breeding of crops, molecular markers for identifying an allele at a rice-blast-resistant Pik locus of rice and use thereof are provided. The Pik gene is re-sequenced, and through sequence polymorphism analysis, identity codes, 3 SNPs, composed of nucleotide types at reverse sites 806, 901 and 4210 of the Pik-1 start codon have been found, which effectively identify Pik, Pike, Pil, Pikm, and Piks. The molecular markers quickly screen the allele type at the Pik locus, obtain an accurate result just by PCR (Polymerase Chain Reaction) and electrophoresis detection, and has high throughput and low cost.

3 Claims, 3 Drawing Sheets

Specification includes a Sequence Listing.

(56) References Cited

OTHER PUBLICATIONS

CN108977568A_Description is English Translation of CN108977568A by Tian Dagang et al. filed Aug. 22, 2018, pub. Dec. 11, 2018 (Year: 2018).*

CN112662804A_Description is English Translation of CN112662804A by Kou Yanjun et al. filed Jan. 25, 2021, pub. Apr. 16, 2024 (Year: 2024).*

CN116640774A_Description is English Translation of CN116640774A by Qi ZhongQiang et al. filed Jun. 14, 2023, pub. Aug. 25, 2023 (Year: 2023).*

CN117778607A_Description is English Translation of CN117778607A by Wang Wenming et al. filed Jul. 27, 2023, pub. Mar. 29, 2024 (Year: 2024).*

CN106048069A_Description is English Translation of CN106048069A by Zhang Zhihong et al. filed Aug. 16, 2016, pub. Oct. 26, 2016 (Year: 2016).*

JP4756334B_Description is English Translation of JP4756334B by Otsubo Kenichi et al. filed Sep. 1, 2005, pub. Aug. 24, 2011 (Year: 2011).*

He et al., 2017. Identification of SNP for rice blast resistance gene Pike and development of the gene-specific markers. Euphytica, 213(3), 61, pp. 1-9. (Year: 2017).*

Imam et al., 2014. Molecular screening for identification of blast resistance genes in North East and Eastern Indian rice germplasm (*Oryza sativa* L.) with PCR based makers. Euphytica, 196(2), pp. 199-211. (Year: 2014).*

Jamshidi et al., 2022. A review of optimization strategies and the advantages and disadvantages of using polymerase chain reaction with confronting two-pair primers (PCR-CTPP) in genomics studies,27(4) pp. 121-132. (Year: 2022).*

Kim et al., 2010. Screening of rice blast resistance genes from aromatic rice germplasms with SNP markers. The Plant Pathology Journal, 26(1), pp. 70-79. (Year: 2010).*

Kim et al., 2011. Screening of the dominant rice blast resistance genes with PCR-based SNP and CAPS marker in aromatic rice germplasm. 한국작물학회지, 56(4), pp. 329-341. (Year: 2011).*

Liu et al., 2025. Development and Application of Pik Locus-Specific Molecular Markers for Blast Resistance Genes in Yunnan Japonica Rice Cultivars. Plants, 14(4), 592, pp. 1-14. (Year: 2025).*

Okada et al., 2018. Identification of QTLs for rice grain size using a novel set of chromosomal segment substitution lines derived from Yamadanishiki in the genetic background of Koshihikari. Breeding Science, 68(2), pp. 210-218. (Year: 2018).*

Okada et al., 2019. Validation of a quantitative trait locus for the white-core expression rate of grain on chromosome 6 in a brewing rice cultivar and development of DNA markers for marker-assisted selection. Breeding Science, 69(3), pp. 401-409. (Year: 2019).*

Patel, S., 2014. Designing Allele Specific Primers: A Bioinformatics Approach. Agrobios Newsletter. Vol XIII (05) pp. 31-32. (Year: 2014).*

Ramkumar et al., 2011. Development and validation of functional marker targeting an InDel in the major rice blast disease resistance gene Pi54 (Pik h). Molecular breeding, 27(1), pp. 129-135. (Year: 2011).*

Tacconi et al., 2010. Polymorphism analysis of genomic regions associated with broad-spectrum effective blast resistance genes for marker development in rice. Molecular breeding, 26(4), pp. 595-617. (Year: 2010).*

Yadav et al., 2017. Use of molecular markers in identification and characterization of resistance to rice blast in India. PloS one, 12(4), e0176236, pp. 1-19. (Year: 2017).*

Yang et al., 2010. Confronting two-pair primer design for enzyme-free SNP genotyping based on a genetic algorithm. BMC bioinformatics, 11(1), 509, pp. 1-11. (Year: 2010).*

Zheng et al., 2016. Genetic mapping and molecular marker development for Pi65 (t), a novel broad-spectrum resistance gene to rice blast using next-generation sequencing. Theoretical and applied genetics, 129(5), pp. 1035-1044. (Year: 2016).*

Chun Zhai et al., "The isolation and characterization of Pik, a rice blast resistance gene which emerged after rice domestication," New Phytologist, vol. 189, pp. 321-334 (2012).

Jing Chen et al., "Pike, a rice blast resistance allele consisting of two adjacent NBS-LRR genes, was identified as a novel allele at the Pik locus," Molecular breeding, vol. 35:117, pp. 1-15 (2015).

Fen Meng et al., "Analysis of natural variation of the rice blast resistance gene Pike and identifcation of a novel allele Pikg," Molecular Genetics and Genomics, vol. 296, pp. 939-952 (May 2021).

Zhang Yu et al., "Selection of molecular marker of resistance genes *Pi-km* locus of rice blast," Journal of Sichuan Agricultural University, vol. 32, No. 3, pp. 252-259 (Sep. 2014).

* cited by examiner

MOLECULAR MARKERS FOR IDENTIFYING ALLELE AT RICE-BLAST-RESISTANT PIK LOCUS OF RICE AND USE THEREOF

CROSS-REFERENCE TO RELATED APPLICATION

The subject application claims priority on Chinese patent application no. 202111532161.1 filed on Dec. 14, 2021 in China. The contents and subject matters of the Chinese priority application is incorporated herein by reference.

REFERENCE TO AN ELECTRONIC SEQUENCE LISTING

The contents of the electronic sequence listing (Name of the File: SequenceListing8022wh.xml; Size: 25,835 bytes; and Date of Creation: Nov. 9, 2022) is herein incorporated by reference in its entirety.

BACKGROUND OF THE INVENTION

Technical Field

The invention belongs to the field of molecular genetic breeding of crops, and relates to molecular markers for identifying an allele at Pik locus of rice and use thereof.

Description of Related Art

Rice is one of the main food crops in China, and its high and stable yield is of great significance for maintaining the food security of China. During the growth process of rice, it may suffer from many diseases and insect damage, of which rice blast can occur in all stages of rice growth and development and has the characteristics of strong epidemicity and wide incidence area. The traditional control of rice blast mainly relies on fungicides, but the long-term use of fungicides will cause the pathogenic bacteria to develop resistance, and also cause environmental pollution, which is not conducive to sustainable development. Breeding practice shows that using excellent resistance resources and genes to breed new rice varieties with broad-spectrum disease resistance is an economical, efficient and environmentally friendly method for controlling rice blast.

At present, through map-based cloning, reverse genetics and other methods, more than 100 rice-blast-resistant genes have been identified from rice, and more than 30 genes of them have been cloned. These genes have the characteristics of clustering, and one gene cluster is distributed on each of rice chromosomes 6, 11, and 12. On the chromosome 11,7 rice-blast-resistant genes (Pik, Pike, Pikh, Pikm, Pikp, Piks, Pil) with broad-spectrum resistance have been cloned. The resistance of these alleles is jointly determined by two CC-NB S-LRR-like genes (Pik-1 and Pik-2) that are closely linked but have opposite transcription directions. Comparing the functional allele sequences of Pik locus of resistant varieties Kusabue (Pik), Tsuyuake (Pikm), K60 (Pikp) and non-functional allele DNA sequences of susceptible varieties Nipponbare, the Pik allelic variants could fall into at least two genome types (N-type and K-type) (Zhai et al., 2012, New Phytologist 189:321-334). At present, the cloned alleles Pik, Pike, Pil, Pikm, Piks, Pikp and Pikh with disease resistance function are all K-haplotype, and there is further differentiation of KM subhaplotypes (Pik, Pike, Pil, Pikm and Piks) and KH subhaplotypes (Pikp and Pikh). Using 215 isolates from Hunan and Jiangxi provinces in China to conduct resistance spectrum analysis, it was found that the resistance frequency of Pike was as high as 86.1%, and the resistance frequency of Pikm and Pil were 50.2% and 48.4%, respectively (Chen et al., 2015, Molecular breeding 35:117). Production practice also shows that genes such as Pik and Pil have strong resistance to many physiological races of rice blast in China, especially in southern rice regions of China. Therefore, the disease resistance gene at the Pik locus has important application value in disease resistance breeding of rice.

In disease resistance breeding of rice, to screen out antigen materials containing functional alleles (Pik, Pike, Pikm, Piks or Pil) of KM subhaplotypes, an allelic analysis method is required, that is, different isolates of Magnaporthe oryzae are used to inoculate antigen materials and analyze their differences in resistance spectrum to identify different alleles. However, the occurrence of rice blast is easily affected by environmental factors, and other resistance genes in the genetic background will have a certain crossover with Pik, Pike, Pikm, Piks or Pil during the resistance-spectrum analysis. This method is time-consuming and complicated and cannot accurately and truly reflect genotypes. Although sequencing of existing materials using sequencing technology has high accuracy, it needs to go through processes such as PCR amplification, gel detection, cloning, sequencing, and sequence alignment analysis, which is time-consuming, costly, and inefficient. With the development of molecular marker technology, the use of molecular markers to identify genes has become a common method in disease resistance breeding. For the Pik site, a research team from South China Agricultural University has developed a set of Piks identification markers (CN Application No. 201210118460.5). This set of molecular markers includes 3 dCAPS markers, but only Piks could be identified by the three markers. The detection process needs to undergo PCR, enzyme digestion, and polyacrylamide gel detection. The research team of Wuhan University developed dCAPS molecular markers d-G1328C and d-A3017T to detect Pike using the specific SNPs in Pike (CN201410794672.4; Chen et al., 2015, Molecular breeding 35:117). However, recent studies have shown that the nucleotide types at the 1328 locus of the coding region of Pikg-1 and the 3017 locus of the coding region of Pikg-2 are the same as those of Pike (Meng et al., 2021, Molecular Genetics and Genomics 296:939-952), so the test results with this molecular marker need to be further verified. The research team from South China Agricultural University recently disclosed a set of inclusive and accurate technical system for identifying and mining the Pik resistance allele family of rice blast (CN202110644560.0), this set of molecular markers can identify 9 alleles including Pik, Pikm, Piks, Pil, Pikp, Pikh, etc. However, for each allele in this set of markers, 1 to 4 allele-specific dCAPS markers need to be used separately for detection, and this method needs to undergo PCR, enzyme digestion, electrophoresis detection and other processes. Other related molecular markers (CN202011566147.9; CN201810055528.7; Zhang Yu et al., 2014, Journal of Sichuan Agricultural University 32:252-259, etc.) designed for the Pik locus cannot identify allele types. In the invention, the applicant provides a set of molecular markers for accurate and efficient identification of Pik, Pike, Pikm, Piks and Pil. The set of markers contains 3 molecular markers in total, and the identification process only needs to go through PCR amplification and gel detection. The method is simple, fast, and low-cost, and can be widely used in rice germplasm resources Pik allele identification and blast-resistant germplasm screening. The method is simple, fast, and low-cost, and can be widely used in Pik allele identification for rice germplasm resources and rice-blast-resistant germplasm screening.

BRIEF SUMMARY OF THE INVENTION

An objective of the invention is to provide a molecular marker primer combination for identifying an allele at a rice-blast-resistant Pik locus of rice, comprising 12 primers in total. Using this primer combination, the nucleotides at 3 SNP sites in Pik loci can be detected, and then the rice germplasm resources containing Pik, Pike, Pikm, Piks or Pil can be screened.

Another objective of the invention is to provide use for identifying an allele type at a rice-blast-resistant Pik locus.

The objectives of the invention are achieved through the following technical solutions:

The applicant re-sequences the Pik gene, and through sequence polymorphism analysis, it is found that identity codes, i.e., 3 SNPs, composed of nucleotide types at reverse loci 806, 901 and 4210 of the Pik-1 start codon, can effectively identify Pik, Pike, Pil, Pikm, and Piks. On this basis, the applicant designed molecular marker primers that can accurately identify Pik, Pike, Pikm, Piks and Pil:

A molecular marker primer combination for identifying an allele at a rice-blast-resistant Pik locus of rice, comprising:

```
                                (SEQ ID NO: 11)
    T806G-F: ATGGTACCGGTGGATCTCGA, (SEQ ID NO: 12)
    T806G-R: CAAGAGTCTCTGTTAGATTGGGACT, (SEQ ID NO: 13)
    806G-F: TCGCAGGTGACCTAAGAGATGAT,
    and (SEQ ID NO: 14)
    806T-R: CCATCACCGACCACCACTTCC;

(SEQ ID NO: 21)
    T901C-F: GTACCGGTGGATCTCGATTC, (SEQ ID NO: 22)
    T901C-R: ATGGTGTGCTAAGTGTATCAGTTAC, (SEQ ID NO: 23)
    901C-F: GTTGCTGGAGGTCAGCATAGC,
    and (SEQ ID NO: 24)
    901T-R: CTCCTTCACATCTTCCATTA;

(SEQ ID NO: 25)
    T4210G-1F: TAATCGATGACATTTGGCATT, (SEQ ID NO: 26)
    T4210G-1R: CCTCAGATAAAGAGGAAGATGG, (SEQ ID NO: 27)
    4210G-R: TGCTATCCTCCAAGACAAGGATCA,
    and (SEQ ID NO: 28)
    4210T-F: GGATCTAGATAATAATGATGCATT.
```

The present invention also provides the use of the above primer combination for identifying the allele type at a rice-blast-resistant Pik locus, which can identify and screen rice germplasm resources containing Pik, Pike, Pikm, Piks or Pil.

Compared with the current technology, the present invention has the following advantages.

1. The Pik gene has been re-sequenced, and through sequence polymorphism analysis, it is found that identity codes, i.e., 3 SNPs, composed of nucleotide types at reverse loci 806, 901 and 4210 of the Pik-1 start codon, can effectively identify Pik, Pike, Pil, Pikm, and Piks. On this basis, the applicant designed molecular markers that can accurately identify Pik, Pike, Pikm, Piks and Pil with strong specificity.

2. The invention makes improvements and innovations on the basis of the PCR with confronting two-pair primers (PCR-CTPP) method. By introducing mismatched bases into an inner primer, the specificity of an inner primer to identify the base type at an SNP site.

3. The molecular markers of the invention can rapidly screen allele types at the Pik loci, and can obtain accurate results just by PCR and electrophoresis detection, and has the characteristics of high throughput and low cost. Traditional allele identification requires rice materials to be planted in a specific environment, and uses multiple single spores for inoculation identification to analyze their resistance spectrum, which is costly and takes a long time. Detecting specific genes by sequencing requires a series of processes such as PCR amplification, electrophoresis detection, and cloning which is costly and insufficient. dCAPS markers designed for SNPs need to undergo PCR amplification, enzyme digestion, electrophoresis detection and other processes, which are cumbersome and costly. The dCAPS markers designed for SNPs need to undergo PCR amplification, enzyme digestion, electrophoresis detection and other processes, which are cumbersome and costly.

BRIEF DESCRIPTION OF THE SEVERAL VIEWS OF THE DRAWINGS

FIG. 1A shows detection electropherogram of a primer combination of T806G-1F/1R, 806G-1F and 806T-1R for gradient PCR amplification of Pik (lanes 1-12) and Pil (lanes 13-24), and the temperature gradient ranges from 50° C. to 70° C.; FIG. 1B shows detection electropherogram of a primer combination of T806G-F/R, 806G-F and 806T-R for gradient PCR amplification of Pik (lanes 1-12) and Pil (lanes 13-24), and the temperature gradient ranges from 50° C. to 70° C.; and FIG. 1C shows electrophoresis detection results of the molecular marker T806G primer combination of T806G-F/R and 806G-F/R for allele identification: M: DL2000 (TaKaRa, Janpan); 1: Xiangzao 143 (Pike); 2: IRBLkm (Pikm); 3: IRBLks-F$_5$ (Piks); 4: IRBLk-ka (Pik); 5: IRBL1-CL (Pil); 6: IRBLkp-K60 (Pikp); 7: IRBLkh-K3 (Pikh).

FIG. 2A shows detection electropherogram of a primer combination of T901C-1F/1R, 901C-1F and 901T-1R for gradient PCR amplification of Pik (lanes 1-12) and Piks (lanes 13-24), and the temperature gradient ranges from 50° C. to 70° C.; FIG. 2B shows detection electropherogram of a primer combination of T901C-F/R, 901C-2F and 901T-2R for gradient PCR amplification of Pik (lanes 1-12) and Piks (lanes 13-24), and temperature gradient ranges from 50° C. to 70° C.; FIG. 2C shows electrophoresis detection results of T901C-F/R, 901C-F and 901T-R for gradient PCR amplification of Pik (lanes 1-12) and Piks (lanes 13-24), and the temperature gradient ranges from 50° C. to 70° C.; FIG. 2D shows electrophoresis detection results of molecular marker T901C primers T901C-F/R and 901C-F/R for allele identification: M: DL2000 (TaKaRa, Janpan); 1: Xiangzao 143 (Pike); 2: IRBLks-F$_5$ (Piks); 3: IRBLkm (Pikm); 4: IRBLk-ka (Pik); 5: IRBL1-CL (Pil); 6: IRBLkp-K60 (Pikp); 7: IRBLkh-K3 (Pikh).

FIG. 3A shows detection electropherograms of a primer combination of T4210G-F/R, 4210T-F and 4210G-R for gradient PCR amplification of Piks (lanes 1-12) and Pik (lanes 13-24), and the temperature gradient ranges from 50° C. to 70° C.; and FIG. 3B shows electrophoresis results of molecular marker T4210G primers T4210G-1F/R, 4210G-R and 4210T-F for allele identification. M: DL2000 (TaKaRa, Janpan); 1: Xiangzao 143 (Pike); 2: IRBLkm (Pikm); 3: IRBLks-F₅ (Piks); 4: IRBLk-ka (Pik); 5: IRBL1-CL (Pil); 6: IRBLkp-K60 (Pikp); 7: IRBLkh-K3 (Pikh).

DETAILED DESCRIPTION OF THE INVENTION

Figure 1A:
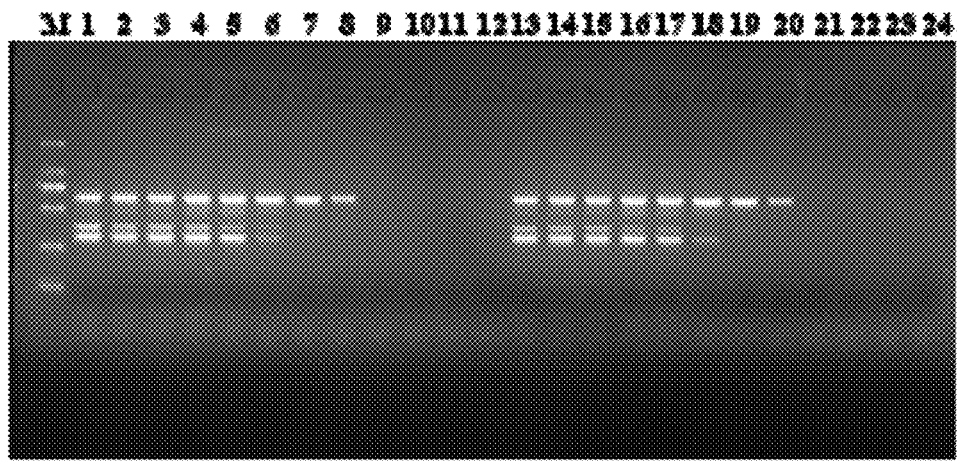
FIGS. 1A to 1C show agarose gel electrophoresis maps for molecular marker T806G optimization and result verification in the present invention, where

The invention will be described in further detail below with reference to the embodiments and the accompanying drawings, but the embodiments of the invention are not limited thereto. Unless otherwise specified, the technical means used in the examples are conventional means well known to those skilled in the art. The rTaq enzyme and dNTP used in the invention were purchased from Takara Bio (Dalian) Co., Ltd., and the others were all conventional biochemical reagents.

EXAMPLE 1

SNP Site Screening

In order to obtain rice antigen materials containing functional alleles (Pik, Pike, Pikm, Piks and Pil) of KM subhaplotypes from backbone parents of hybrid rice, the applicant designed sequencing primers based on the genome sequence of K-haplotype (Table 1), and verified the specificity of the primers using the donor material DNA of Pik, Pike, Pil, Pikm, Piks, Pikp and Pikh respectively.

TABLE 1

| Sequence information of primers for Pik-1 sequencing in the invention | | |
|---|---|---|
| Name of primer | Forward primer sequence (5'-3') | Reverse primer sequence (5'-3') |
| K1 | tactgttaaccttgctctaat taca (SEQ ID NO: 1) | aggaagtcttcacagtgctaa ct (SEQ ID NO: 2) |
| K2 | caagattcagaacacgactcc (SEQ ID NO: 3) | tatcatgtagagttgcggagg (SEQ ID NO: 4) |
| K3 | aacagggaaatgcagagctag (SEQ ID NO: 5) | tcttgggaatggactttctgat (SEQ ID NO: 6) |

The CTAB method has been used to extract the DNA of 263 rice germplasm resources from a wide range of sources, including IR24, R287, Teqing, and IR72, and carried out PCR using the above primers, and it was found that only 108 rice materials such as IR24, R287, Basmatis, Jia 814, Qianxin 124, C418 and Centauro were K-haplotypes at the Pik locus. Subsequently, the applicant sequenced the Pik-1 allelic variants in the above 108 materials, and screened a total of 28 rice lines containing Pik, Pike, Pikm, Piks or Pil (Table 2).

TABLE 2

| Rice antigen materials screened by sequencing technology | |
|---|---|
| Disease resistance gene | Material name |
| Pik | Shaoniejing, Hejiang 19, R069, Ejing 17, Kongyu 131 |
| Pike | Zaoyou 143, Zao 143/898B |

TABLE 2-continued

| Rice antigen materials screened by sequencing technology | |
|---|---|
| Disease resistance gene | Material name |
| Pikm | Wai 95-122, DEDALO, Chenghui 178, R433, Chenghui 727, Chenghui 9348, Lemont, TR2, LABELLE |
| Piks | Barilla, CRM360-37-8, IDRA, YR6-100-9, Longke large-grain rice, Yueguang, Daohuaxiang, Xin 13, Qiuguang, Xin 15 |
| Pil | C101LAC, IR38 |

In order to find a method for rapid and efficient screening of rice antigen materials carrying functional alleles (Pik, Pike, Pikm, Piks and Pil) of KM subhaplotypes, the applicant compared the genome sequences of Pik-1 allelic variants in the above 108 rice materials with Pik, Pike, Pil, Pikm, Piks, Pikp and Pikh, and obtained a total of 225 SNP sites in Pik-1 and 15 insertion/deletion sites. Since no SNP sites specific to Pik, Pike, Pikm, Piks and Pil were found, the applicant conducted a permutation and combination analysis of the SNP sites, and finally found that identity codes composed of nucleotide types at 806, 901 and 4210 sites in the CDS of Pik-1 can effectively differentiate Pik, Pike, Pil, Pikm and Piks. At sites 806, 901 and 4210, the nucleotide type of Pik is GTT, the nucleotide type of Pike is TTT, the nucleotide type of Pil is TTG, the nucleotide type of Pikm is GTG, the nucleotide type of Piks is GCG.

EXAMPLE 2

Design and Result Verification of Molecular Markers T806G

According to the design method of two pairs of cross primers, the applicant first designed two-sided universal primers T806G-1F/-1R for SNP T/G at the site 806 to amplify the flanking SNP fragments. Subsequently, the applicant designed primers 806G-1F and 806T-1R for T and G at the site 806, respectively, in which the sequence of 806G-1F completely matched the sequences of Pike and Pil (806-G), and the sequence of 806T-1R completely matched sequences of Pik, Pikm and Piks (806-T) (Table 3). The applicant mixed the above-mentioned 4 primers in equal volumes as primers in PCR, and used the genomic DNAs from the donor materials of Pil and Pik as templates to carry out gradient PCR, and the PCR temperature gradient was set within a range of 50° C. to 70° C. Agarose gel electrophoresis showed that the combination of the above four primers could not distinguish Pil from Pik (FIG. 1A), and an unexpected band appeared below the expected consensus fragment. The above results show that the binding ability between primers 806G-1F and 806T-1R directly designed by software and DNA templates is too strong, resulting in the amplified fragments not having specificity. Therefore, flanking SNP sequences cannot be directly used as SNP site-specific primers.

Figure 1B:
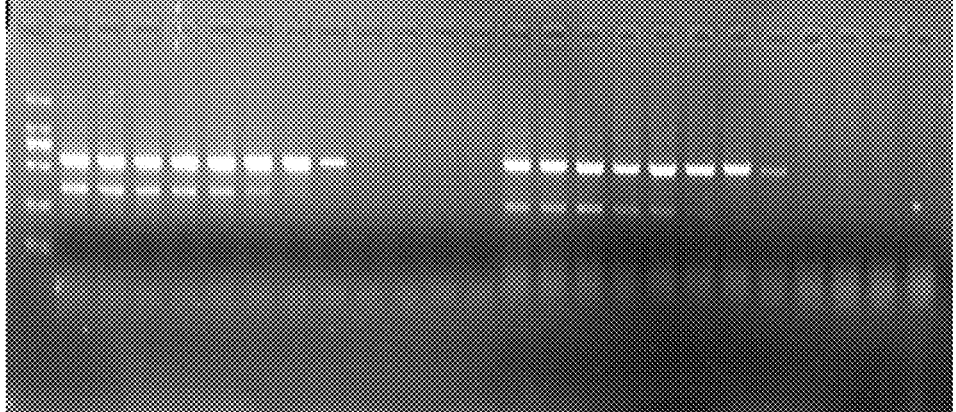
Figure 1C:
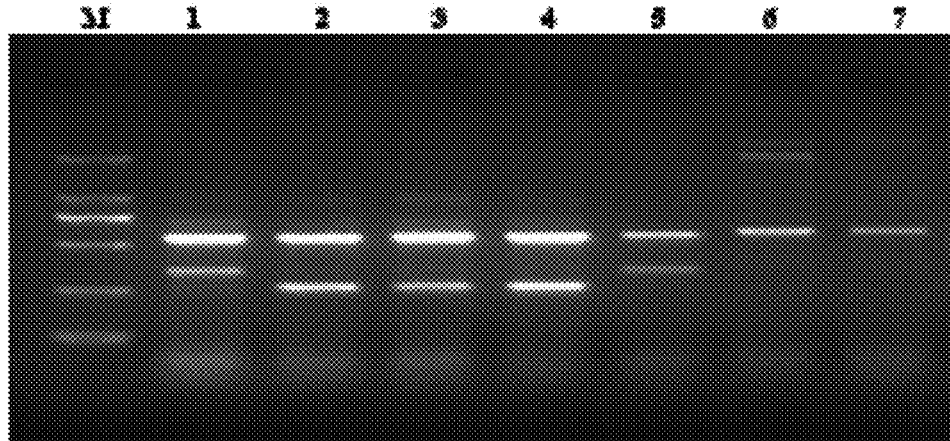

Subsequently, the applicant redesigned the universal primers and named them T806G-F/R (Table 3). And the forward bases at the SNP sites in the 806G-1F and 806T-1R primer sequences were modified. Through continuous attempts, it was finally found that specific PCR products could be obtained by gradient PCR detection after modifying the penultimate 4th base in 806G-1F from C to T and modifying the penultimate 3rd and 4th bases in 806T-1R from AA to TT (the primers having the bases changed were named 806G-F and 806T-R, respectively) (FIG. 1B). Moreover, the molecular markers T806G was verified with the genomic DNAs of gene donor rice materials of Pik, Pike, Pil, Pikm, Piks, Pikp and Pikh (FIG. 1C). It was found that markers T806G amplified DNA fragments with lengths of 558 bp and 339 bp (banding pattern was assigned as 1) from genomic DNAs of Xiangzao 143 (Pike) and IRBL1-CL (Pil), DNA fragments with lengths of 558 bp and 262 bp (banding pattern was assigned as 2) from IRBLkm (Pikm), IRBLks-F₅ (Piks) and IRBLk-ka (Pik), and DNA fragments with lengths of 589 bp (banding pattern was assigned as 3) from IRBLkp-K60 (Pikp) and IRBLkh-K3 (Pikh).

TABLE 3

Sequence information of primers for optimization of molecular markers
T806G

| Name of primer | Primer sequence (5'-3') | Remarks |
|---|---|---|
| T806G-1F | agggagcagtgatgcttca (SEQ ID NO: 7) | |
| T806G-1R | gaaattcacatatggatttcacc (SEQ ID NO: 8) | |
| 806G-1F | tcgccggtgacctaagagacgat (SEQ ID NO: 9) | |
| 806T-1R | ccatcaccgaccaccacaacc (SEQ ID NO: 10) | |
| T806G-F | atggtaccggtggatctcga (SEQ ID NO: 11) | Molecular marker T806G |
| T806G-R | caagagtctctgttagattgggact (SEQ ID NO: 12) | Annealing temperature |
| 806G-F | tcgcaggtgacctaagagatgat (SEQ ID NO: 13) | 52° C. |
| 806T-R | ccatcaccgaccaccacttcc (SEQ ID NO: 14) | |

Note:
Bold nucleotide symbols indicate bases introducing mismatches

EXAMPLE 3

Design and Result Verification of Molecular Markers T901C

Figure 2A:
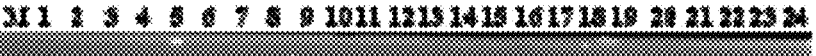
FIGS. 2A to 2D show agarose gel electrophoresis maps for molecular marker T901C optimization and result verification in the present invention, where
Figure 2A:
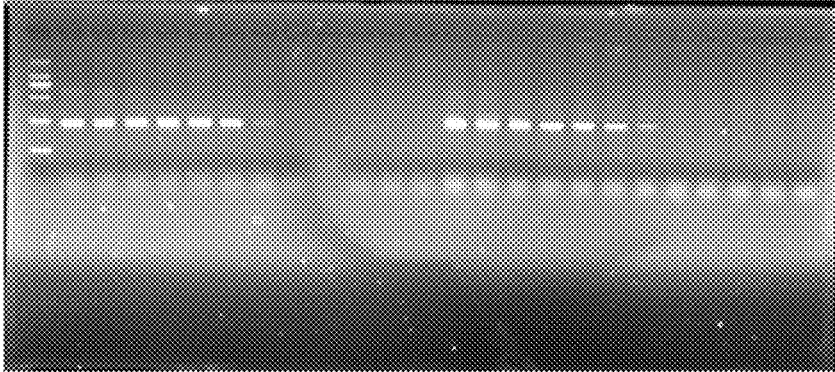
Figure 2B:
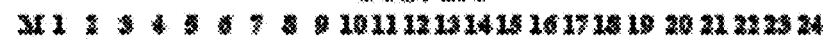
Figure 2B:
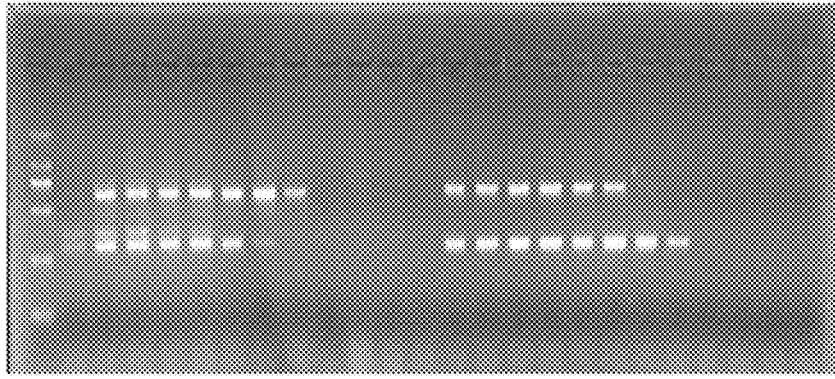

For SNP 901C/T, the applicant first designed universal primers T901C-1F/-1R to amplify the flanking sequences of the SNP site, and also designed specific primers 901T-1F and 901C-1R for the base types T and C at the site 901, respectively, in which the sequence of 901T-1F completely matched the sequences of Pik, Pil, Pikm and Pike (901-T), and the sequence of 901C-1R differed only by a single base from the sequences of Piks, Pikp and Pikh (901-C). The above-mentioned 4 primers in equal volumes were mixed to carry out PCR using DNAs from the donor materials of Pik and Piks as templates. Agarose gel electrophoresis showed that the consensus primer did not amplify the expected band, and the band patterns of Pik and Piks were the same. (FIG. 2A). The applicant then redesigned the universal primers and named them T901C-F/-R, and the SNP site-specific primers 901C-2F and 901T-2R were re-synthesized by modifying the penultimate 4th base in the 901C-1F sequence from T to A and deleting the terminal base A in 901T-1R. PCR detection results show that the universal primers T901C-F/-R have specific amplification, while the primer 901C-2F has too strong binding ability to the template, resulting in that fragments that only appear in base type C at site 901 can be amplified in both Pik and Piks (FIG. 2B).

Figure 2C:
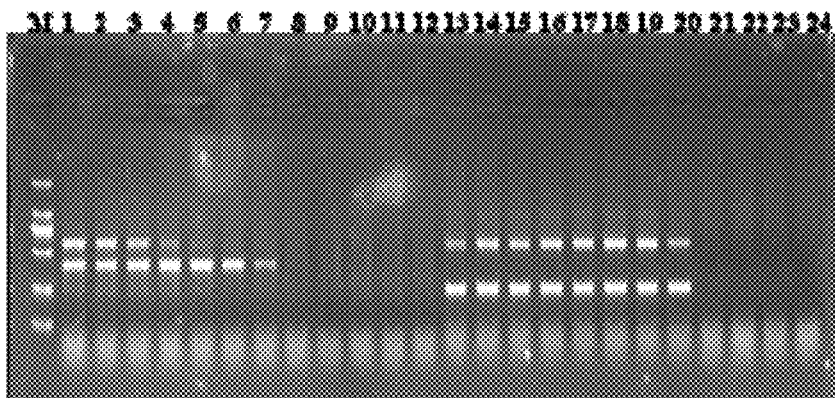

Subsequently, the applicant adjusted the sequence of the SNP site-specific primer, and finally found that the primers 901C-F and 901T-R newly synthesized after modifying the CAs at sites 17 and 18 in the 901C-2F primer sequence to ATs and deleting the base T at site 1 in 901T-R cooperated with T901C-F/-R to amplify the fragment with specificity (FIG. 2C). The sequence information of primers is shown in Table 4.

Figure 2D:
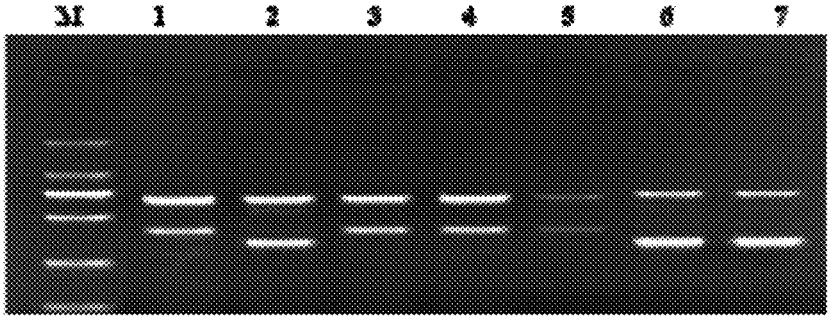

Moreover, the molecular markers T901C was verified with the genomic DNAs of gene donor rice materials of Pik, Pike, Pil, Pikrn, Piks, Pikp and Pikh. It was found that markers T901C amplified DNA fragments with lengths of 554 bp and 358 bp (banding pattern was assigned as 1) from genomic DNAs of Xiangzao 143 (Pike), IRBL1-CL (Pil), IRBLkm (Pikm) and IRBLk-ka (Pik), DNA fragments with lengths of 554 bp and 241 bp (banding pattern was assigned as 2) from IRBLks-F₅ (Piks), and DNA fragments with lengths of 630 bp and 241 bp (banding pattern was assigned as 3) from IRBLkp-K60 (Pikp) and IRBLkh-K3 (Pikh) (FIG. 2D).

TABLE 4

Sequence information of primers for optimization of molecular markers
T901C

| Name of primer | Primer sequence (5'-3') | Remarks |
|---|---|---|
| T901C-1F | atggcgctgccaataaatt (SEQ ID NO: 15) | |
| T901C-1R | aagagtctctgttagattgggactg (SEQ ID NO: 16) | |
| 901T-1R | tctccttcacatcttccttta (SEQ ID NO: 17) | |

TABLE 4-continued

Sequence information of primers for optimization of molecular markers T901C

| Name of primer | Primer sequence (5'-3') | Remarks |
|---|---|---|
| 901C-1F | ttgctggaggtcagccaagca<br>(SEQ ID NO: 18) | |
| 901C-2F | gttgctggaggtcagccaagc<br>(SEQ ID NO: 19) | |
| 901T-2R | tctccttcacatcttccatta<br>(SEQ ID NO: 20) | |
| T901C-F | gtaccggtggatctcgattc<br>(SEQ ID NO: 21) | Molecular marker T901C<br>Annealing temperature |
| T901C-R | atggtgtgctaagtgtatcagttac<br>(SEQ ID NO: 22) | 53° C. |
| 901C-F | gttgctggaggtcagcatagc<br>(SEQ ID NO: 23) | |
| 901T-R | ctccttcacatcttccatta<br>(SEQ ID NO: 24) | |

Note:
Bold nucleotide symbols indicate bases introducing mismatches

EXAMPLE 4

Design and Result Verification of Molecular Markers T4210G

Figure 3A:
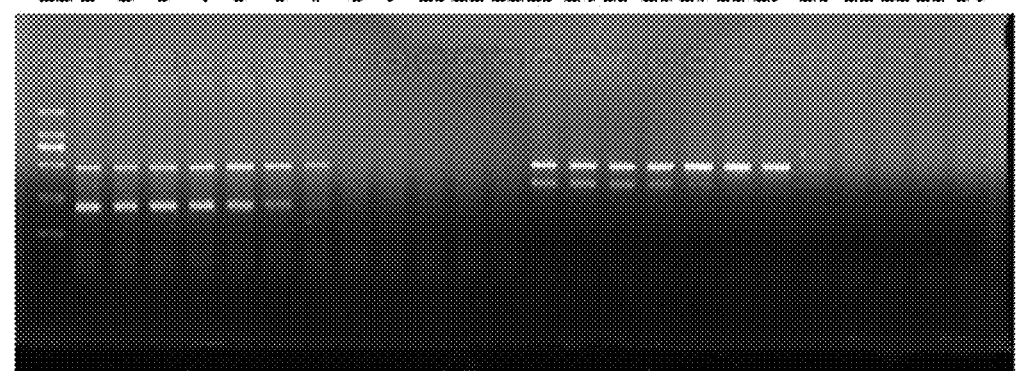
FIGS. 3A and 3B show agarose gel electrophoresis maps for verifying design results of molecular markers T4210G in the present invention, where

For SNP 4210G/T, the applicant first designed primers T4210G-F/R (Table 5) to amplify the flanking sequences of the SNP site. Based on the nucleotide sequence of 4210G and its forward 23 bases, the penultimate 3rd nucleotide was modified from T to A as the primer sequence of 4210G-F. For the reverse primer, 3 nucleotides were modified based on the nucleotide sequence of 1 forward base and 22 reverse bases of 4210G, and the sequence was reverse complemented as the primer sequence of 4210T-R. The above-mentioned 4 primers in equal volumes were mixed to carry out PCR using DNAs from the donor materials of Pik and Piks as templates. Agarose gel electrophoresis showed that this molecular marker could distinguish Pik from Piks (FIG. 3A).

Figure 3B:
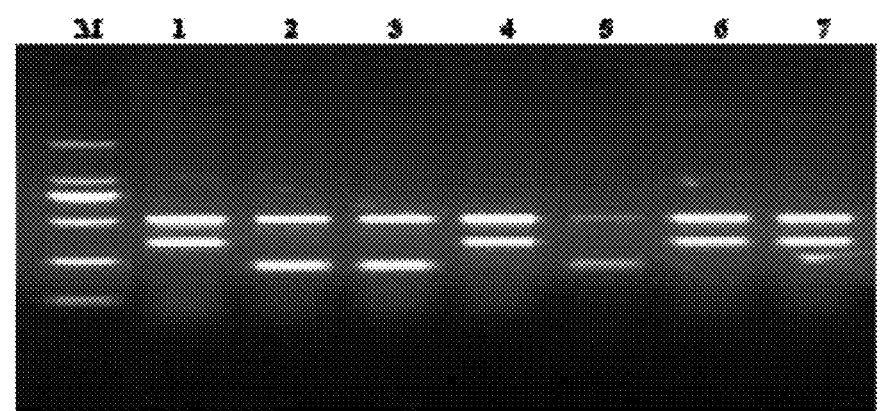

The applicant has verified the molecular markers T901C using the genomic DNAs from the gene donor rice materials of Pik, Pike, Pil, Pikrn, Piks, Pikp and Pikh. The molecular markers T4210G amplified DNA fragments with lengths of 467 bp and 310 bp (banding pattern was assigned as 1) from Xiangzao 143 (Pike), IRBLk-ka (Pik), IRBLkp-K60 (Pikp) and IRBLkh-K3 (Pikh) and DNA fragments with lengths of 467 bp and 203 bp (banding pattern was assigned as 2) from IRBLkm (Pikm), IRBL1-CL (Pil) and IRBLks-F$_5$ (Piks) (FIG. 3B).

TABLE 4

Primer sequence information of molecular markers T4210G

| Name of primer | Primer sequence (5'-3') | Remarks |
|---|---|---|
| T4210G-1F | taatcgatgacatttggcatt<br>(SEQ ID NO: 25) | Molecular marker T4210G<br>Annealing temperature |
| T4210G-1R | cctcagataaagaggaagatgg<br>(SEQ ID NO: 26) | 52° C. |
| 4210G-R | tgctatcctccaagacaaggatca<br>(SEQ ID NO: 27) | |
| 4210T-F | ggatctagataataatgatgcatt<br>(SEQ ID NO: 28) | |

Note:
Bold nucleotide symbols indicate bases introducing mismatches

Figure 4:
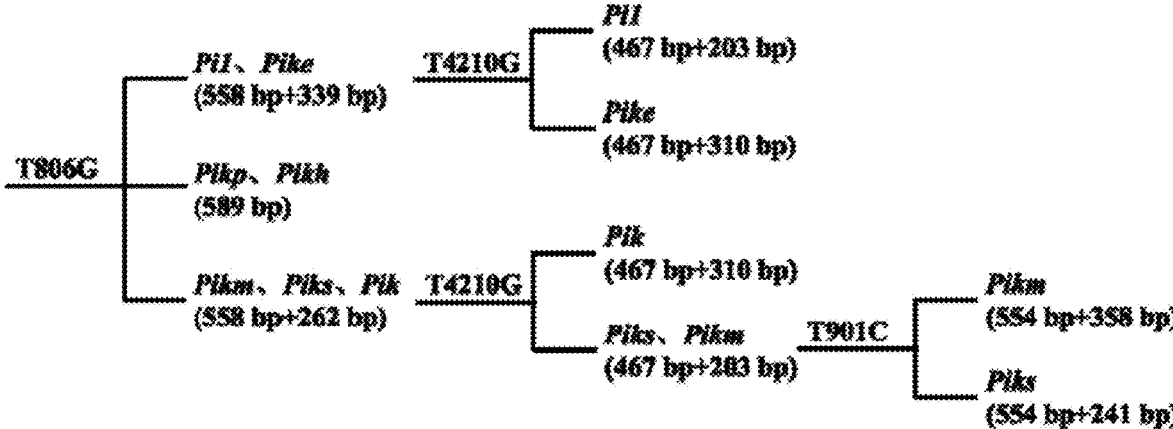
FIG. 4 shows the molecular markers screened according to the present invention for identifying Pik, Pike, Pikm, Piks and Pil carrying lines.

The above examples show that Pik, Pike, Pikrn, Piks and Pil can be effectively identified according to the detection results of molecular markers T806G, T901C and T4210G. In actual use, the appropriate molecular marker combination can be selected according to the needs. For example, if it is required to screen antigens containing Pike, Pil or Pik, the molecular markers T806G and T4210G are used; if it is required to screen antigens containing Pikm or Piks, molecular markers T806G, T901C and T4210G are used. The schematic diagram of the molecular markers for identifying Pik, Pike, Pikm, Piks and Pil antigens is shown in FIG. 4.

EXAMPLE 5

Use of Molecular Markers for Screening
Rice-Blast-Resistant Germplasm Resources (1) Biomaterials: 263 rice germplasm resources from a wide range of sources are shown in Table 6.

(2) Rice DNA extraction and primers: The genomic DNAs of the above materials were extracted by CTAB method, and the molecular markers were T806G, T901C and T4210G developed in Example 1. The primer sequences are shown in Tables 3 to 5.

The primers for T806G were:

```
                                          (SEQ ID NO: 11)
T806G-F: ATGGTACCGGTGGATCTCGA,
and (SEQ ID NO: 12)
T806G-R: ATGGTACCGGTGGATCTCGA;

(SEQ ID NO: 13)
806G-F: TCGCAGGTGACCTAAGAGATGAT,
and (SEQ ID NO: 14)
806T-R: CCATCACCGACCACCACTTCC.
```

The primers for T901C were:

```
                                          (SEQ ID NO: 21)
T901C-F: GTACCGGTGGATCTCGATTC,
and (SEQ ID NO: 22)
T901C-R: ATGGTGTGCTAAGTGTATCAGTTAC;

(SEQ ID NO: 23)
901C-F: GTTGCTGGAGGTCAGCATAGC,
and
```

-continued
```
                                          (SEQ ID NO: 24)
901T-R: CTCCTTCACATCTTCCATTA.
```

The primers for 4210G were:

```
                                          (SEQ ID NO: 25)
T4210G-1F: TAATCGATGACATTTGGCATT,
and (SEQ ID NO: 26)
T4210G-1R: CCTCAGATAAAGAGGAAGATGG;

(SEQ ID NO: 27)
4210G-R: TGCTATCCTCCAAGACAAGGATCA,
and (SEQ ID NO: 28)
4210T-F: GGATCTAGATAATAATGATGCATT.
```

(3) PCR and Agarose Gel Electrophoresis Detection

The PCR reaction volume was 10 μL, and the annealing temperatures of the markers were set as shown in Tables 3 to 5, and 30 cycles were set. Amplification products were detected in 1.5%-2% agarose gel and the results were recorded.

(4) Result Record and Genotype Evaluation

After obtaining the electropherograms of 263 rice germplasm resources amplified by 3 molecular markers, the banding pattern of each material at each molecular marker was recorded according to the description in Examples 2 to 4 to obtain the banding pattern data of the materials and determine the genotypes, and the banding pattern of the material that has not been amplified excluding DNA quality problems was recorded as "-". The banding pattern data and genotyping results of the materials are shown in Table 6.

(5) Genotyping Results and Analysis

Through molecular marker detection, from 263 rice germplasm resources, the applicant detected 5 materials (Shaoniejing, Hejiang 19, R069, Ejing 17 and Kongyu 131) with the banding pattern of 211 at the molecular markers T806G, T4210G and T901C, indicating that these 5 materials carried Pik. 2 materials (C101LAC and IR38) had a banding pattern of 121 at 3 markers, indicating that these 2 materials carried Pil. 2 materials (Zaoyou 143 and Zao 143/898B) had a banding pattern of 111 at 3 markers, indicating that these 2 materials carried Pike. 9 materials (Wai 95-122, DEDALO, Chenghui 178, R433, Chenghui 727, Chenghui 9348, Lemont, TR2 and LABELLE) had a banding pattern of 221 at 3 markers, indicating that these 9 materials carried Pikm. Another 10 materials (Barilla, CRM360-37-8, IDRA, YR6-100-9, Longke large-grain rice, Yueguang, Daohuaxiang, Xin 13, Qiuguang, Xin 15) had a banding pattern of 222, indicating that they carried Piks. The above results are consistent with those in Example 1.

TABLE 6

| | | | | | | | | | |
|---|---|---|---|---|---|---|---|---|---|
| Banding pattern record of rice germplasm resources detected by molecular markers and genotype evaluation | | | | | | | | | |
| Material name | T806G | T4210G | T901C | Gene | Material name | T806G | T4210G | T901C | Gene |
| Xiangzao 143 (Pike) | 1 | 1 | 1 | Pike | Ezao 18 | 3 | 1 | 3 | |
| IRBLks-F5 (Piks) | 2 | 2 | 2 | Piks | 6303S | — | — | — | |
| IRBLkm (Pikm) | 2 | 2 | 1 | Pikm | Gang B | 3 | 1 | 3 | |
| IRBLk-ka (Pik) | 2 | 1 | 1 | Pik | 509S | — | — | — | |
| IRBL1-CL (Pil) | 1 | 2 | 1 | Pil | Runzhu537 | — | — | — | |
| IRBLkp-K60 (Pikp) | 3 | 1 | 3 | Pikp | 71068 | 2 | 1 | 2 | |

TABLE 6-continued

Banding pattern record of rice germplasm resources detected
by molecular markers and genotype evaluation

| Material name | T806G | T4210G | T901C | Gene | Material name | T806G | T4210G | T901C | Gene |
|---|---|---|---|---|---|---|---|---|---|
| IRBLkh-K3 (Pikh) | 3 | 1 | 3 | Pikh | Shaoniejing | 2 | 1 | 1 | Pik |
| 9311 | — | — | — | | Jiahe218 | — | — | — | |
| Teqing | — | — | — | | Jiahe228 | — | — | — | |
| R8006 | — | — | — | | Milyang83 | — | — | — | |
| Mianhui725 | — | — | — | | Ly9505 | 3 | 1 | 3 | |
| IR38 | 1 | 2 | 1 | Pil | Zaoyou143 | 1 | 1 | 1 | Pike |
| IR6 | — | — | — | | Yuanfengzao | 3 | 1 | 3 | |
| Nantehao | — | — | — | | Guanghui380 | — | — | — | |
| IR72 | — | — | — | | Guanghui880 | 3 | 1 | 3 | |
| X21 | — | — | — | | 05R10 | — | — | — | |
| #018 | — | — | — | | 05R54 | — | — | — | |
| #608 | — | — | — | | R1 | 3 | 1 | 3 | |
| Hua-1 | — | — | — | | R2 | 3 | 1 | 3 | |
| Minghui86 | 3 | 1 | 3 | | R3 | — | — | — | |
| Kanghui63 | — | — | — | | R4 | 3 | 1 | 3 | |
| Luhui63 | — | — | — | | R5 | 3 | 1 | 3 | |
| Shenghui11 selected | — | — | — | | R6 | — | — | — | |
| CDR22 | 2 | 1 | 2 | | 158B | — | — | — | |
| Duohui No. 1 | — | — | — | | Moroberekan | — | — | — | |
| Fuhui838 | — | — | — | | B505 | — | — | — | |
| Mianhui734 | — | — | — | | B242 | 3 | 1 | 3 | |
| Wanhui88 | — | — | — | | B243 | 3 | 1 | 3 | |
| #6078 | 3 | 1 | 3 | | B245 | 3 | 1 | 3 | |
| Shengtai No. 1 | — | — | — | | B288 | 3 | 1 | 3 | |
| Manghui | — | — | — | | B289 | 3 | 1 | 3 | |
| Zhenhui084 | — | — | — | | B290 | 3 | 1 | 3 | |
| NA9311 | — | — | — | | B294 | 3 | 1 | 3 | |
| R5014 | 3 | 1 | 3 | | 05CR92 | 3 | 1 | 3 | |
| Enhui69 | — | — | — | | 05CR170 | — | — | — | |
| R1128 | — | — | — | | Guoyou12 | 3 | 1 | 3 | |
| Huazhan | — | — | — | | Zhaiyeqing No. 8 | 3 | 1 | 3 | |
| R6102 | — | — | — | | STAR BONNET | — | — | — | |
| Peiai645 | 3 | 1 | 3 | | #92-4 | — | — | — | |
| YuetaiB | — | — | — | | Barilla | 2 | 2 | 2 | Piks |
| II-32B | — | — | — | | Ezao No. 6 | — | — | — | |
| Jin23B | 3 | 1 | 3 | | Ezao No. 11 | 3 | 1 | 3 | |
| IR58025B | 3 | 1 | 3 | | Zhenguiai | — | — | — | |
| WuxiangB | 2 | 1 | 2 | | Hejiang19 | 2 | 1 | 1 | Pik |
| Bo-B | — | — | — | | Tetep | — | — | — | |
| JufengB | 3 | 1 | 3 | | Digu | 3 | 1 | 3 | |
| C101A51 | — | — | — | | C101LAC | 1 | 2 | 1 | Pil |
| 75-1-127 | — | — | — | | NJ5-375 | — | — | — | |
| N07CR20 | — | — | — | | Yueguang | 2 | 2 | 2 | Piks |
| N07CR38 | — | — | — | | P8823 | 3 | 1 | 3 | |
| N07CR80 | — | — | — | | Ningjing No. 3 | — | — | — | |
| Wai95-122 | 2 | 2 | 1 | Pikm | DianR | 3? | 1 | 3 | |
| Enhui218 | 3 | 1 | 3 | | Xiangshui117 | — | — | — | |
| CBB23 | — | — | — | | R069 | 2 | 1 | 1 | Pik |
| IRBB21 | — | — | — | | Wuxianggeng14 | — | — | — | |
| Feng986 | — | — | — | | Nannong-8 | — | — | — | |
| IRBB66 | — | — | — | | Nangeng45 | — | — | — | |
| IR65482-7 | — | — | — | | Nipponbare | — | — | — | |
| CO39 | — | — | — | | Shuhui527 | — | — | — | |
| CRM360-37-8 | 2 | 2 | 2 | Piks | Minghui63 | — | — | — | |
| DEDALO | 2 | 2 | 1 | Pikm | IR8 | 2 | 1 | 2 | |
| IDRA | 2 | 2 | 2 | Piks | IR36 | 3 | 1 | 3 | |
| KHAO LAH MAO LII | — | — | — | | IR1327 | — | — | — | |
| KHAO LANG PEN SAW | — | — | — | | MY23 | 3 | 1 | 3 | |
| KHAO NIIP LONG | — | — | — | | MBP98 | — | — | — | |
| BLUE BELLE | — | — | — | | Gui630 | — | — | — | |
| LEBONNET | 3 | 1 | 3 | | Shenghui747 | — | — | — | |
| YR6-100-9 | 2 | 2 | 2 | Piks | Ce49 | 3 | 1 | 3 | |
| TUPA 147 | — | — | — | | Ce64 | 3 | 1 | 3 | |
| BORO 120 | — | — | — | | Zihui100 | — | — | — | |
| BASMATIS 370 | 3 | 1 | 3 | | PESOS | — | — | — | |
| SUWEON 287 | 2 | 1 | 2 | | PC311 | 2 | 1 | 2 | |
| MILYANG 51 | 3 | 1 | 3 | | R288 | — | — | — | |
| PTB33 | 3 | 1 | 3 | | J413 | — | — | — | |

TABLE 6-continued

| Banding pattern record of rice germplasm resources detected by molecular markers and genotype evaluation | | | | | | | | | |
|---|---|---|---|---|---|---|---|---|---|
| Material name | T806G | T4210G | T901C | Gene | Material name | T806G | T4210G | T901C | Gene |
| T12 | — | — | — | | 908 | 3 | 1 | 3 | |
| SUDURVI 305 | — | — | — | | IRCe-80-1-1 | — | — | — | |
| MAHADIKWEE | 3 | 1 | 3 | | #955 | 3 | 1 | 3 | |
| OVARKARUPPAN | — | — | — | | Xin15 | 2 | 2 | 2 | Piks |
| SINNA KARUPPAN | 3 | 1 | 3 | | Chenghui178 | 2 | 2 | 1 | Pikm |
| Kuruhondarawala | — | — | — | | R53021 | 3 | 1 | 3 | |
| LAC23 | — | — | — | | 09R-1 | — | — | — | |
| IR64 | 3 | 1 | 3 | | 09R-3 | — | — | — | |
| 99C0770 | — | — | — | | R433 | 2 | 2 | 1 | Pikm |
| 114# | — | — | — | | R207 | 3 | 1 | 3 | |
| 116# | 3 | 1 | 3 | | R402 | — | — | — | |
| 156# | — | — | — | | Chenghui727 | 2 | 2 | 1 | Pikm |
| 10Gang58 | — | — | — | | Chenghui9348 | 2 | 2 | 1 | Pikm |
| Sizhongkang | — | — | — | | Gang46B | 2 | 1 | 2 | |
| Hui10 | 3 | 1 | 3 | | Zhenshan97B | — | — | — | |
| Hui10-g | — | — | — | | ZhongjiuB | 3 | 1 | 3 | |
| Changzao No. 2 | 3 | 1 | 3 | | V20B | 3 | 1 | 3 | |
| Efeng28 | — | — | — | | MaxieB | — | — | — | |
| Hefengnian | — | — | — | | D62B | — | — | — | |
| Xianhuangnian | — | — | — | | 898B | 3 | 1 | 3 | |
| Shennongxiangnian | 3 | 1 | 3 | | 05CR89B | — | — | — | |
| Shuijing No. 3 | — | — | — | | EjinB | 3 | 1 | 3 | |
| Wanxian No. 9 | — | — | — | | Zao143/898B | 1 | 1 | 1 | Pike |
| HR73 | — | — | — | | Yue4B | — | — | — | |
| HR78 | — | — | — | | K2B(K2A) | — | — | — | |
| HR83 | — | — | — | | A4B | 3 | 1 | 3 | |
| HR117 | — | — | — | | Huanghuanian | — | — | — | |
| HR132 | — | — | — | | 9119 | — | — | — | |
| N07CR84 | — | — | — | | Yuexiangnian | — | — | — | |
| Zhong3B | 3 | 1 | 3 | | Xiangdao | — | — | — | |
| Sirio | — | — | — | | Molixiangnian | — | — | — | |
| Oveso | — | — | — | | High-protein xiangnian | — | — | — | |
| Dardo | — | — | — | | Jianzhen No. 2 | — | — | — | |
| Xin13 | 2 | 2 | 2 | Piks | Ejing17 | 2 | 1 | 1 | Pik |
| SR | — | — | — | | BG304 | 3 | 1 | 3 | |
| Longke large-grain rice | 2 | 2 | 2 | Piks | Bataixiangnian | — | — | — | |
| Erlicun | — | — | — | | Xiangzaoxian No. 21 | — | — | — | |
| I76S | 3 | 1 | 3 | | Daohuaxiang | 2 | 2 | 2 | Piks |
| TianfengB | 3 | 1 | 3 | | Kongyu131 | 2 | 1 | 1 | Pik |
| Wusansimiao | — | — | — | | Huhan No. 3 | — | — | — | |
| Lijiang Xintuanheigu | 3 | 1 | 3 | | Yangdao No. 4 | — | — | — | |
| HuazhanHB | — | — | — | | Whenshengnuo | — | — | — | |
| Zhonghaixiang No. 1 | — | — | — | | Ewan No. 13 | — | — | — | |
| Jindaoxiang | — | — | — | | Weng229 | 3 | 1 | 3 | |
| Liyuanzhan No. 1 | — | — | — | | Enhui58 | — | — | — | |
| Guiyu No. 9 | — | — | — | | 814B | 3 | 1 | 3 | |
| Liushayouzhan | — | — | — | | Lemont | 2 | 2 | 1 | Pikm |
| Lvhan No. 1 | 3 | 1 | 3 | | New Bonnel | — | — | — | |
| Zhenghan No. 6 | — | — | — | | B292 | 3 | 1 | 3 | |
| R900 | — | — | — | | Miyang83 | — | — | — | |
| Shuhui498 | 3 | 1 | 3 | | 149-3 | — | — | — | |
| Y5-657 | 3 | 1 | 3 | | Gunong2923 | — | — | — | |
| ShijingB | — | — | — | | 05CR185 | — | — | — | |
| Taizhong No. 1 | — | — | — | | Guojisuo No. 1 | — | — | — | |
| TR2 | 2 | 2 | 1 | Pikm | #02428 | — | — | — | |
| 09B316 | 3 | 1 | 3 | | Forbiprotife | 2 | 1 | 2 | |
| LABELLE | 2 | 2 | 1 | Pikm | Qiuguang | 2 | 2 | 2 | Piks |
| COLOMBIA 2 | — | — | — | | IR24 | 2 | 1 | 2 | |
| R287 | 2 | 1 | 3 | | Basmatis | 2 | 1 | 2 | |
| Jia814 | 2 | 1 | 2 | | Qianxin124 | 2 | 1 | 2 | |
| C418 | 2 | 1 | 2 | | Centauro | 2 | 1 | 2 | |

Note:
Xiangzao 143 (Pike), IRBL1-CL (Pil), IRBLkm (Pikm), IRBLk-ka (Pik), IRBLkp-K60 (Pikp) and IRBLkh-K3 (Pikh) are donor materials of Pike, Pil, Pikm, Pik, Pikp and Pikh, respectively.

The above-mentioned embodiments are preferred embodiments of the invention, but the embodiments of the invention are not limited by the above-mentioned embodiments, and any other changes, modifications, substitutions, combinations, and simplifications made without departing 5 from the spirit and principle of the invention should be interpreted as equivalent substitutions and are included within the scope of the invention.

We claim:

1. A molecular marker primer combination for identifying an allele at a rice-blast-resistant Pik locus of rice, comprising one or more of the following primer combinations:

(1) a first primer combination consisting of a primer sequence comprising SEQ ID NO: 11, a primer sequence comprising SEQ ID NO: 12, a primer sequence comprising SEQ ID NO: 13, and a primer sequence comprising SEQ ID NO: 14;

(2) a second primer combination consisting of a primer sequence comprising SEQ ID NO: 21, a primer sequence comprising SEQ ID NO: 22, a primer sequence comprising SEQ ID NO: 23, and a primer sequence comprising SEQ ID NO: 24; and (3) a third primer combination consisting of a primer sequence comprising SEQ ID NO: 25, a primer sequence comprising SEQ ID NO: 26, a primer sequence comprising SEQ ID NO: 27, and a primer sequence comprising SEQ ID NO: 28.

2. A method for identifying an allele type at the rice-blast-resistant Pik locus of rice, comprising providing the molecular marker primer combination as described in claim 1 in a polymerase chain reaction (PCR) test of a rice DNA and amplifying a fragment of the rice DNA by the molecular marker primer combination, and identifying the allele type at the rice-blast-resistant Pik locus of rice based on sizes of the amplified fragments of the rice DNA, wherein the amplification of the rice DNA with the first primer combination indicates presence of the allele types of Pil or Pike with two amplified fragment bands at 558 bp and 339 bp, Pikm, Piks, or Pik with two amplified fragment bands at 558 bp and 262 bp, or Pikp or Pikh with a single amplified fragment band at 589 bp;

the amplification of the rice DNA with the second primer combination indicates the allele types of Pik or Pike with two amplified fragment bands at 467 bp and 310 bp, or Pil, Piks, or Pikm with two amplified fragment bands at 467 bp and 203 bp;

the amplification of the rice DNA with the third primer combination indicates the allele type of Pikm with two amplified fragment bands at 554 bp and 358 bp, or Piks with two amplified fragment bands at 554 bp and 241 bp.

3. A testing kit for identifying a rice-blast-resistant allele type present at the Pik locus of rice, comprising the molecular marker primer combination as described in claim 1.

* * * * *

SEQUENCE LISTING

```
Sequence total quantity: 28
SEQ ID NO: 1              moltype = DNA  length = 25
FEATURE                   Location/Qualifiers
source                    1..25
                          mol_type = other DNA
                          organism = synthetic construct
SEQUENCE: 1
tactgttaac cttgctctaa ttaca                                    25

SEQ ID NO: 2              moltype = DNA  length = 23
FEATURE                   Location/Qualifiers
source                    1..23
                          mol_type = other DNA
                          organism = synthetic construct
SEQUENCE: 2
aggaagtctt cacagtgcta act                                      23

SEQ ID NO: 3              moltype = DNA  length = 21
FEATURE                   Location/Qualifiers
source                    1..21
                          mol_type = other DNA
                          organism = synthetic construct
SEQUENCE: 3
caagattcag aacacgactc c                                        21

SEQ ID NO: 4              moltype = DNA  length = 21
FEATURE                   Location/Qualifiers
source                    1..21
                          mol_type = other DNA
                          organism = synthetic construct
SEQUENCE: 4
tatcatgtag agttgcggag g                                        21

SEQ ID NO: 5              moltype = DNA  length = 21
FEATURE                   Location/Qualifiers
source                    1..21
                          mol_type = other DNA
                          organism = synthetic construct
SEQUENCE: 5
aacagggaaa tgcagagcta g                                        21

SEQ ID NO: 6              moltype = DNA  length = 22
FEATURE                   Location/Qualifiers
source                    1..22
                          mol_type = other DNA
                          organism = synthetic construct
SEQUENCE: 6
tcttgggaat ggactttctg at                                       22

SEQ ID NO: 7              moltype = DNA  length = 19
FEATURE                   Location/Qualifiers
source                    1..19
                          mol_type = other DNA
                          organism = synthetic construct
SEQUENCE: 7
agggagcagt gatgcttca                                           19

SEQ ID NO: 8              moltype = DNA  length = 23
FEATURE                   Location/Qualifiers
source                    1..23
                          mol_type = other DNA
                          organism = synthetic construct
SEQUENCE: 8
gaaattcaca tatggatttc acc                                      23

SEQ ID NO: 9              moltype = DNA  length = 23
FEATURE                   Location/Qualifiers
```

-continued

```
source                  1..23
                        mol_type = other DNA
                        organism = synthetic construct
SEQUENCE: 9
tcgccggtga cctaagagac gat                                      23

SEQ ID NO: 10           moltype = DNA   length = 21
FEATURE                 Location/Qualifiers
source                  1..21
                        mol_type = other DNA
                        organism = synthetic construct
SEQUENCE: 10
ccatcaccga ccaccacaac c                                        21

SEQ ID NO: 11           moltype = DNA   length = 20
FEATURE                 Location/Qualifiers
source                  1..20
                        mol_type = other DNA
                        organism = synthetic construct
SEQUENCE: 11
atggtaccgg tggatctcga                                          20

SEQ ID NO: 12           moltype = DNA   length = 25
FEATURE                 Location/Qualifiers
source                  1..25
                        mol_type = other DNA
                        organism = synthetic construct
SEQUENCE: 12
caagagtctc tgttagattg ggact                                    25

SEQ ID NO: 13           moltype = DNA   length = 23
FEATURE                 Location/Qualifiers
source                  1..23
                        mol_type = other DNA
                        organism = synthetic construct
SEQUENCE: 13
tcgcaggtga cctaagagat gat                                      23

SEQ ID NO: 14           moltype = DNA   length = 21
FEATURE                 Location/Qualifiers
source                  1..21
                        mol_type = other DNA
                        organism = synthetic construct
SEQUENCE: 14
ccatcaccga ccaccacttc c                                        21

SEQ ID NO: 15           moltype = DNA   length = 19
FEATURE                 Location/Qualifiers
source                  1..19
                        mol_type = other DNA
                        organism = synthetic construct
SEQUENCE: 15
atggcgctgc caataaatt                                           19

SEQ ID NO: 16           moltype = DNA   length = 25
FEATURE                 Location/Qualifiers
source                  1..25
                        mol_type = other DNA
                        organism = synthetic construct
SEQUENCE: 16
aagagtctct gttagattgg gactg                                    25

SEQ ID NO: 17           moltype = DNA   length = 21
FEATURE                 Location/Qualifiers
source                  1..21
                        mol_type = other DNA
                        organism = synthetic construct
SEQUENCE: 17
tctccttcac atcttccttt a                                        21

SEQ ID NO: 18           moltype = DNA   length = 21
FEATURE                 Location/Qualifiers
source                  1..21
                        mol_type = other DNA
                        organism = synthetic construct
SEQUENCE: 18
ttgctggagg tcagccaagc a                                        21

SEQ ID NO: 19           moltype = DNA   length = 21
```

-continued

```
FEATURE                 Location/Qualifiers
source                  1..21
                        mol_type = other DNA
                        organism = synthetic construct
SEQUENCE: 19
gttgctggag gtcagccaag c                                          21

SEQ ID NO: 20           moltype = DNA   length = 21
FEATURE                 Location/Qualifiers
source                  1..21
                        mol_type = other DNA
                        organism = synthetic construct
SEQUENCE: 20
tctccttcac atcttccatt a                                          21

SEQ ID NO: 21           moltype = DNA   length = 20
FEATURE                 Location/Qualifiers
source                  1..20
                        mol_type = other DNA
                        organism = synthetic construct
SEQUENCE: 21
gtaccggtgg atctcgattc                                            20

SEQ ID NO: 22           moltype = DNA   length = 25
FEATURE                 Location/Qualifiers
source                  1..25
                        mol_type = other DNA
                        organism = synthetic construct
SEQUENCE: 22
atggtgtgct aagtgtatca gttac                                      25

SEQ ID NO: 23           moltype = DNA   length = 21
FEATURE                 Location/Qualifiers
source                  1..21
                        mol_type = other DNA
                        organism = synthetic construct
SEQUENCE: 23
gttgctggag gtcagcatag c                                          21

SEQ ID NO: 24           moltype = DNA   length = 20
FEATURE                 Location/Qualifiers
source                  1..20
                        mol_type = other DNA
                        organism = synthetic construct
SEQUENCE: 24
ctccttcaca tcttccatta                                            20

SEQ ID NO: 25           moltype = DNA   length = 21
FEATURE                 Location/Qualifiers
source                  1..21
                        mol_type = other DNA
                        organism = synthetic construct
SEQUENCE: 25
taatcgatga catttggcat t                                          21

SEQ ID NO: 26           moltype = DNA   length = 22
FEATURE                 Location/Qualifiers
source                  1..22
                        mol_type = other DNA
                        organism = synthetic construct
SEQUENCE: 26
cctcagataa agaggaagat gg                                         22

SEQ ID NO: 27           moltype = DNA   length = 24
FEATURE                 Location/Qualifiers
source                  1..24
                        mol_type = other DNA
                        organism = synthetic construct
SEQUENCE: 27
tgctatcctc caagacaagg atca                                       24

SEQ ID NO: 28           moltype = DNA   length = 24
FEATURE                 Location/Qualifiers
source                  1..24
                        mol_type = other DNA
                        organism = synthetic construct
SEQUENCE: 28
ggatctagat aataatgatg catt                                       24
```